(12) United States Patent
Pagan

(10) Patent No.: US 6,604,525 B2
(45) Date of Patent: Aug. 12, 2003

(54) LARYNGEAL MASK AIRWAYS AND THEIR MANUFACTURE

(75) Inventor: Eric Pagan, Hythe (GB)

(73) Assignee: Smiths Group PLC, London (GB)

( * ) Notice: Subject to any disclaimer, the term of this patent is extended or adjusted under 35 U.S.C. 154(b) by 92 days.

(21) Appl. No.: 09/847,324

(22) Filed: May 3, 2001

(65) Prior Publication Data

US 2001/0015207 A1 Aug. 23, 2001

Related U.S. Application Data

(63) Continuation of application No. 09/231,822, filed on Jan. 15, 1999.

(30) Foreign Application Priority Data

Feb. 17, 1998 (GB) .............................................. 9803199

(51) Int. Cl.$^7$ .............................................. A61M 16/00
(52) U.S. Cl. .............................. 128/207.15; 128/207.14; 425/526
(58) Field of Search ................... 128/207.15, 207.14, 128/204.18, 898, 200.24; 425/383, 384, 404, 522, 526, 533, 536, 542, 547, 535, DIG. 110, 245, 247; 264/239, 340, 405, 454, 457, 500, 521, 535

(56) References Cited

U.S. PATENT DOCUMENTS

| | | | | |
|---|---|---|---|---|
| 5,297,547 A | * | 3/1994 | Brain | 128/207.15 |
| 5,305,743 A | * | 4/1994 | Brain | 128/207.15 |
| 5,979,445 A | * | 11/1999 | Neame et al. | 128/207.15 |

FOREIGN PATENT DOCUMENTS

| | | |
|---|---|---|
| EP | 0 448 878 A2 | 10/1991 |
| EP | 0 489 507 A1 | 6/1992 |
| EP | 0 712 638 A1 | 5/1996 |
| EP | 0 865 798 A2 | 9/1998 |
| GB | 2 298 797 A | 9/1996 |
| WO | WO 97/12641 | 4/1997 |

* cited by examiner

*Primary Examiner*—Glenn K. Dawson
(74) *Attorney, Agent, or Firm*—Connolly Bove Lodge & Hutz LLP

(57) ABSTRACT

The mask of a laryngeal mask assembly has a mount and an integral cuff at the patient end of a tube. The mount is of a thermoplastic material and the cuff is made by blow moulding from the material of the mount. A separate retaining plate seals an edge of the cuff with the mount and traps an inflation tube extending from the cuff to the inflation line of the tube.

14 Claims, 2 Drawing Sheets

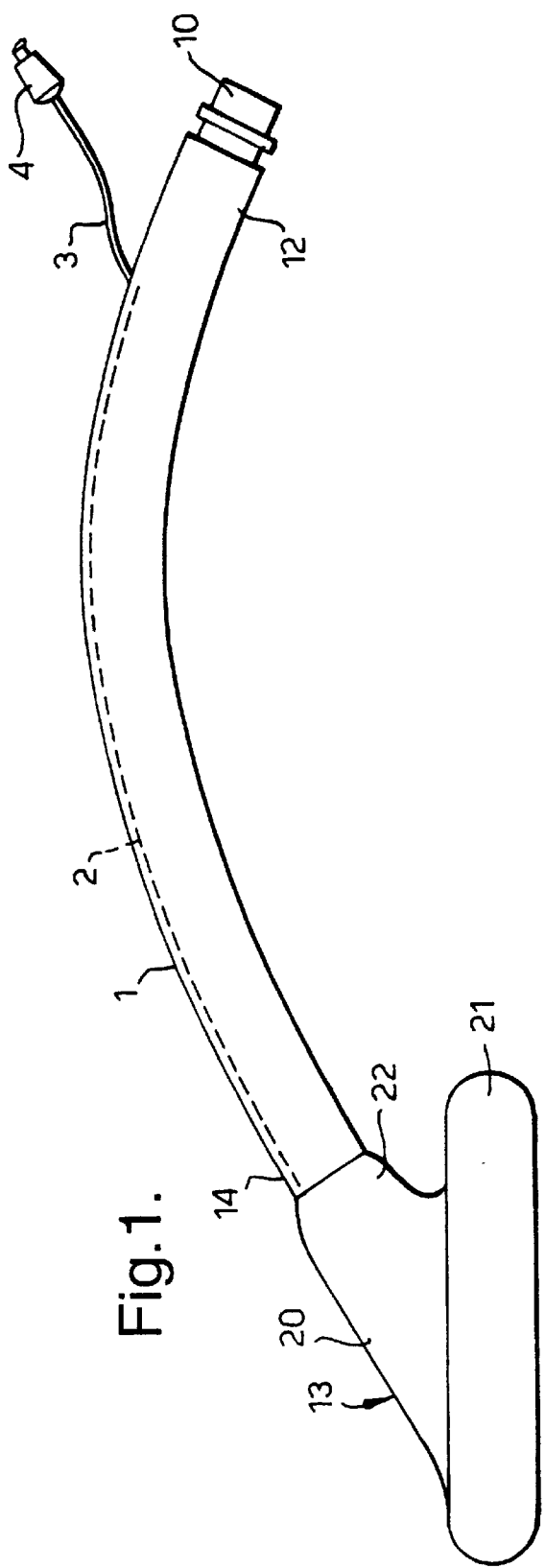
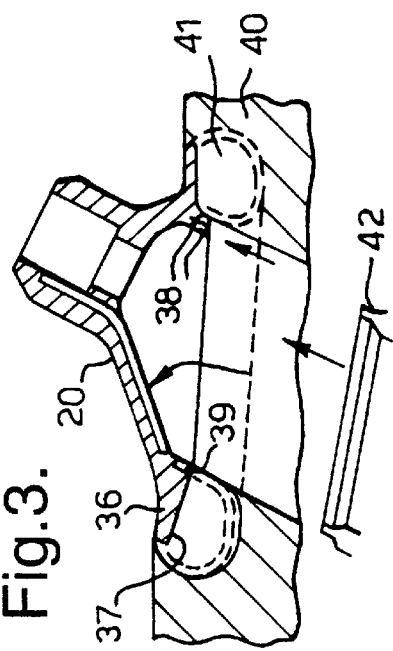
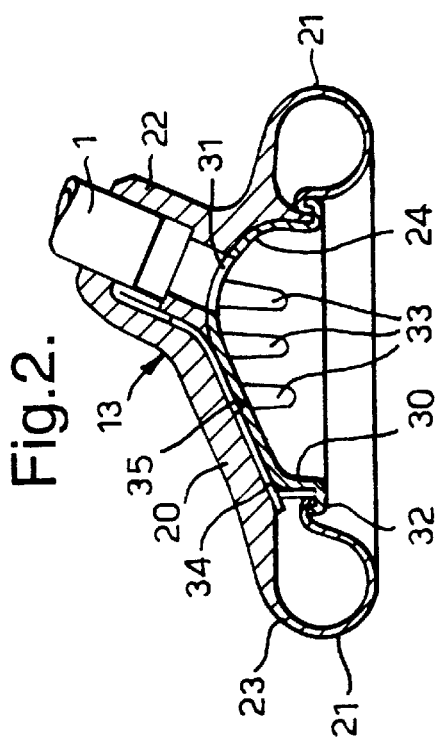

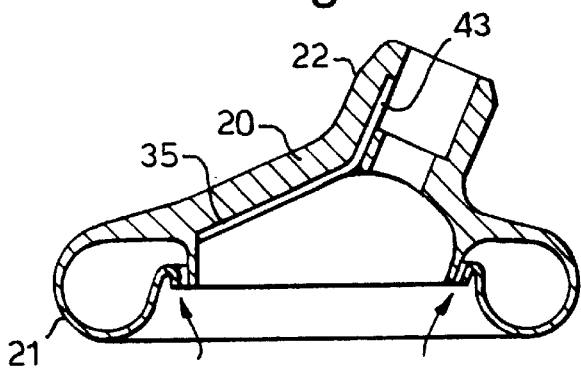
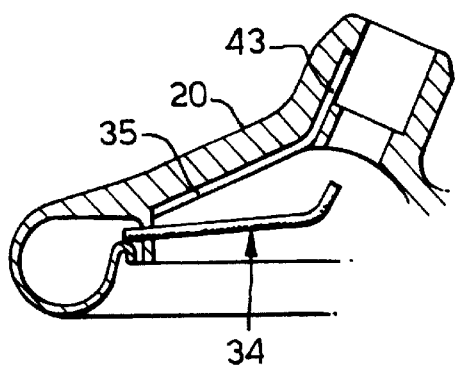
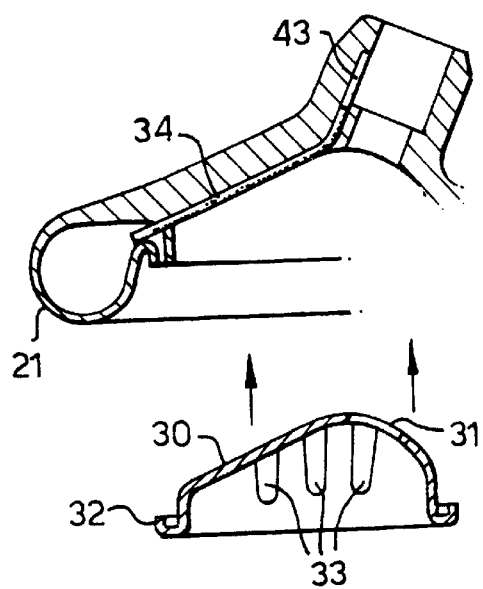
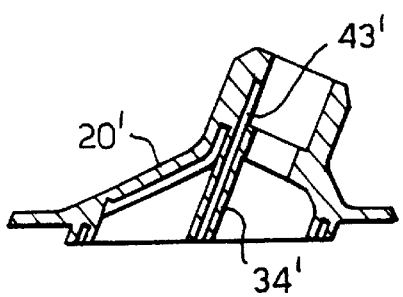
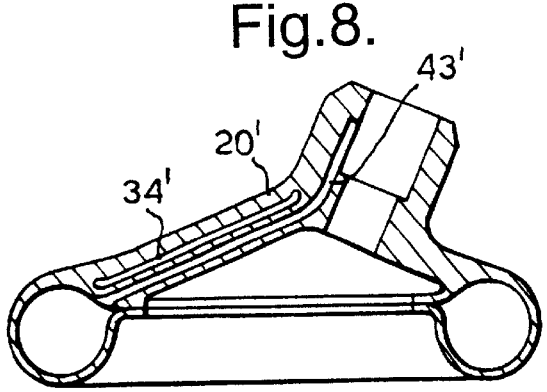
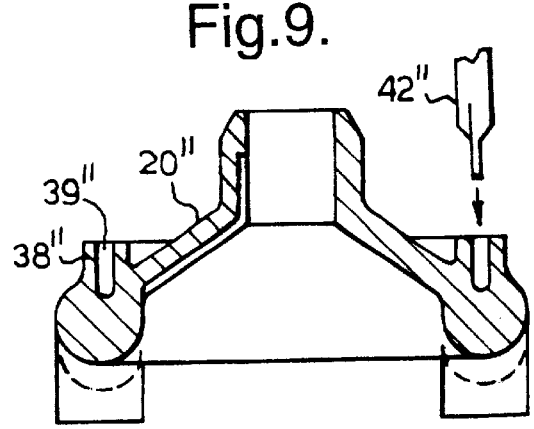

LARYNGEAL MASK AIRWAYS AND THEIR MANUFACTURE

CROSS-REFERENCE TO RELATED APPLICATION

This is a continuation of copending application Ser. No. 09/231,822 filed Jan. 15, 1999 entitled "Laryngeal Masks Airways and Their Manufacture."

BACKGROUND OF THE INVENTION

This invention relates to laryngeal mask airways and their manufacture.

It is common practice to use an airway known as a laryngeal mask for administering anaesthetic and ventilation gases to a patient. These airways comprise a tube with an inflatable mask or cuff at one end, the tube being inserted in the patient's mouth so that one end is located in the hypopharynx and so that the mask forms a seal in this region with the surrounding tissue. Laryngeal masks are described in, for example, U.S. Pat. Nos. 5,355,879, 5,305,743, 5,297,547, 5,282,464, GB 2267034, U.S. Pat. No. 5,249,571, 5,241,956, 5,303,697, GB 2249959, GB 2111394, EP 448878, U.S. Pat. No. 4,995,388, gb2205499 GB 2128561 and GB 2298797.

Laryngeal masks have several advantages over endotracheal tubes, which are longer and seal with the trachea below the vocal folds. It can be difficult, however, to manufacture the patient end of the mask at low cost.

BRIEF SUMMARY OF THE INVENTION

It is an object of the present invention to provide an improved laryngeal mask assembly and method of manufacture.

According to one aspect of the present invention there is provided a laryngeal mask assembly comprising an elongate tube and a mask portion at the patient end of the tube, the mask portion including a mount member of generally elliptical shape having an opening therethrough communicating with the patient end of the tube and a hollow cuff member extending around the mount member, the cuff member being formed integrally from the mount member.

The mount member and the cuff member are preferably made from the same thermoplastic material, the cuff member being blow moulded with a thinner wall than the mount member. The mask portion may include an inflation tube extending along a groove in the mount member. The assembly preferably includes a retaining plate arranged to retain an edge of the cuff member. The mask portion may include a plurality of surface formations, such as ribs, arranged as epiglottis guides. The cuff member may contain a resilient foam.

According to another aspect of the present invention there is provided a method of manufacture of a laryngeal mask assembly including the steps of providing an elongate tube having a mount member at its patient end, the mount member being of generally elliptical shape and having an opening therethrough communicating with the patient end of the tube, and forming from the material of the mount member a hollow cuff member extending around the mount member.

The mount member and the cuff member are preferably made from the same thermoplastic material, the cuff member being blow moulded with a thinner wall than the mount member. The method preferably includes the step of sealing an edge of the cuff member with the mount member by means of a retaining plate. The mount member may either be preformed prior to being placed in a mould tool for blow moulding of the cuff member or the mount member may be moulded in a cavity, the cavity then being enlarged and the cuff member being subsequently blow moulded in the enlarged cavity.

According to a further aspect of the present invention there is provided a laryngeal mask assembly manufactured by a method according to the other aspect of the present invention.

A laryngeal mask airway assembly and its method of manufacture, according to the present invention, will now be described, by way of example, with reference to the accompanying drawings.

BRIEF DESCRIPTION OF THE DRAWINGS

FIG. 1 is a side elevation view of the assembly;

FIG. 2 is an enlarged cross-sectional view of the patient end of the assembly;

FIG. 3 is a cross-sectional view of the mask at a preliminary stage of manufacture;

FIGS. 4 to 6 are cross-sectional views of the mask at subsequent stages of manufacture;

FIGS. 7 and 8 are cross-sectional views showing stages in an alternative manufacture of a mask; and FIG. 9 is a cross-sectional view showing a preliminary stage of another alternative manufacture of a mask.

DETAILED DESCRIPTION OF THE PREFERRED EMBODIMENTS

With reference to FIGS. 1 and 2, the assembly comprises a bendable tube 1 of a plastics material, such as PVC, with a coupling 10 at its machine end 12. The tube 1 is curved along its length and has a mask portion 13 at its patient end 14.

The tube 1 is extruded with an inflation lumen 2 within its wall. The lumen 2 is connected towards the machine end of the assembly to an inflation line 3 with an inflation indicator and connector 4. The opposite, patient end of the inflation lumen 2 communicates with the mask portion 13.

The mask portion 13 comprises a relatively stiff mount member 20 and an integral cuff member 21 both formed integrally with one another from a thermoplastic material, such as PVC. The rear, machine end of the mount member 20 has a cylindrical sleeve 22 attached at the patient end 14 of the tube 1, such as by insert moulding the sleeve about the end of the tube. The forward, patient end 23 of the mount member 20 is of an inverted dish shape with a generally elliptical or egg-shape outline and with a concave recess 24.

The cuff member 21 is considerably thinner than the mount member 20 and provides a hollow annulus extending around the patient side face of the mount member. A separate, moulded retaining plate 30 is attached to the patient side of the mount member, in the concave recess 24 and within the outline of the cuff 21. The retaining plate 30 is of dome shape with an aperture 31 aligned with the bore through the sleeve 22, and hence the tube 1. Around the outer edge of the plate 30 a rearwardly-extending lip 32 overlaps the edge of the cuff member 21. The patient-side face of the plate 30 preferably has surface formations 33 in the form of ribs or the like, to act as epiglottis guides. A short inflation tube 34 extends in a groove 35 on the patient-side of the mount 20, where it is held in place by the retaining plate 30. One end of the tube 34 projects into the cuff 21; the opposite end communicates with the forward end of the inflation lumen 2 in the tube 1.

The stages of manufacture of the assembly will now be described with reference to FIGS. 3 to 6. FIG. 3 shows the mount member 20 before formation of the cuff member 21, the forward end of the mount member terminating with a relatively thick, stiff, radially-extending flange 36. The forward surface 37 of the flange 36 is flat except for two short, forwardly-projecting coaxial walls 38 formed around the inside of the flange and separated from one another by a small gap, so as to form a small annular channel 39. The mount member 20 is placed in a heated injection mould tool 40 having an annular cavity 41 beneath the flange 36 defining the desired shape of the cuff 21. An annular blowing ring 42 is brought into the tool 40 to locate in the channel 39. Air supplied through the blowing ring 42 causes the material of the flange 36, softened by the heat of the tool 40, to be blow moulded to the shape of the cavity 41, that is, to the shape shown in FIG. 4.

A small aperture is formed through the inner one of the walls 38, into the cuff 21, such as with a heated spike (not shown), and one end of the inflation tube 34 is pushed through the aperture into the cuff and bonded in place, as shown in FIG. 5. The tube 34 is then laid in the groove 35 and its other end bonded into a short passage 43 in the mount 20, which opens into the inflation lumen 2 in the tube, as shown in FIG. 6.

The inner end of the cuff 21 is unattached by the blow moulding process, because of the presence of the blowing ring 42. The cuff 21 is sealed by attaching the retaining plate 30 and bonding this to the forward side of mount 20, such as by heat sealing, solvent, adhesive or by a mechanical clip connection.

Instead of using a separate inflation tube, a tube 34' could be formed integrally with the mount 20', extending from the short passage 43' communicating with the inflation lumen 2, as shown in FIG. 7. The tube 34' is joined with the cuff 21' after the blow moulding step, as shown in FIG. 8.

FIG. 9 shows an alternative method of blow moulding the cuff member in which the mount 20" is moulded initially with a ring 38" projecting from its rear surface, the ring 38" having an annular channel 39" or a number of holes to receive a blowing ring or blowing pins 42". Pressure applied through the blowing ring or pins 42" blows the forward part of the mount forwardly into a cavity appropriately shaped to form the desired cuff member.

The mount may be preformed in one mould and subsequently blow moulded to form the cuff in a different mould, as described above. Alternatively, the mount and cuff could be formed in the same mould, this having a movable cavity so that it can be enlarged to enable both operations to be carried out one after the other.

The cuff could be filled with an open cell resilient foam added through the blowing ring or pin following the blowing process. In this way, the cuff would have a naturally inflated or expanded state and would be sucked down for insertion and removal by applying negative pressure to the inflation line.

The present invention can reduce considerably the manual assembly operations needed to make a laryngeal mask assembly. This enables costs to be minimized so that the assembly can be provided as a single-use, disposable device.

What I claim is:

1. A method of making a laryngeal mask comprising:
    providing an elongate tube having a mount member at a patient end of the elongate tube, said mount member being of generally elliptical shape and having an opening therethrough in communication with the patient end of said tube;
    forming a hollow cuff member from said mount member, wherein forming the hollow cuff member comprises:
        heating said mount member in a mould so that material of the mount member flows and moulds into the hollow cuff member, wherein the hollow cuff member extends around said mount member.

2. The method of claim 1, wherein forming the hollow cuff member comprises:
    blow moulding the cuff member to have a thinner wall than said mount member.

3. The method of claim 2, comprising:
    providing a retaining plate; and
    sealing an edge of said hollow cuff member with said mount member using said retaining plate.

4. The method of claim 1, wherein said mount member is preformed prior to being placed in a mould tool for blow moulding of said hollow cuff member.

5. The method of claim 1, wherein forming said hollow cuff member comprises:
    moulding said mount member into a cavity; and
    enlarging said cavity and blow molding said hollow cuff member in the enlarged cavity.

6. The method of claim 1, comprising:
    aligning a channel in the mount member with a blowing ring of an injection mold tool.

7. The method of claim 1, comprising:
    forming an aperture in the hollow cuff member;
    pushing an inflation tube through the aperture;
    placing the inflation tube in a groove in the mount member; and
    bonding an end of the inflation tube into a passage in the mount member.

8. The method of claim 1, wherein providing the mount member comprises:
    providing a mount member with an integral inflation tube extending from a passage in the mount member.

9. The method of claim 8, comprising:
    joining the inflation tube with the hollow cuff member.

10. The method of claim 1, wherein providing the mount member comprises:
    providing a mount member with a ring projecting from a rear surface of the mount member.

11. The method of claim 10, wherein forming the hollow cuff comprises:
    applying pressure to the ring to blow a forward part of the mount member forwardly into a cavity.

12. The method of claim 11, wherein providing the mount member comprises:
    providing a mount member with an annular channel in the ring, the channel being shaped to receive a blowing ring or pins used to blow the forward part of the member forwardly into the cavity.

13. The method of claim 1, comprising:
    filling the hollow cuff member with foam.

14. The method of claim 1, wherein providing a mount member comprises:
    providing a mount member of a thermoplastic material.

* * * * *